US 6,733,533 B1

(12) United States Patent
Lozier (10) Patent No.: US 6,733,533 B1
(45) Date of Patent: May 11, 2004

(54) ARTIFICIAL SPINAL DISC (75) Inventor: Antony Lozier, Warsaw, IN (US)

(73) Assignee: Zimmer Technology, Inc., Chicago, IL (US)

(*) Notice: Subject to any disclaimer, the term of this patent is extended or adjusted under 35 U.S.C. 154(b) by 0 days.

(21) Appl. No.: 10/299,521

(22) Filed: Nov. 19, 2002

(51) Int. Cl.$^7$ .................................................. A61F 2/44
(52) U.S. Cl. ...................................... 623/17.12; 606/61
(58) Field of Search ............................. 623/17.11, 17.12, 623/17.15, 17.16, 23.54; 606/61

(56) References Cited

U.S. PATENT DOCUMENTS

| | | | | |
|---|---|---|---|---|
| 3,867,728 A | * | 2/1975 | Stubstad et al. | 623/17.16 |
| 4,772,287 A | * | 9/1988 | Ray et al. | 623/17 |
| 4,978,355 A | * | 12/1990 | Frey et al. | 623/16 |
| 5,171,281 A | * | 12/1992 | Parsons et al. | 623/17 |
| 5,192,326 A | * | 3/1993 | Bao et al. | 623/17 |
| 6,187,043 B1 | * | 2/2001 | Ledergerber | 623/8 |
| 6,419,704 B1 | * | 7/2002 | Ferree | 623/17.12 |
| 6,447,543 B1 | * | 9/2002 | Studer et al. | 623/17.11 |
| 2002/0077701 A1 | * | 6/2002 | Kuslich | 623/17.12 |

OTHER PUBLICATIONS

Anderson, CE. Spondylochisis Following Spine Fusion. J Bone Joint Surg 1956; 38A: 1142–1146.

Andersson GBJ, Brown MD, Dvorak J. Herzog RJ, et al. Consensus Summary on the Diagnosis and Treatment of Lumbar Disk Herniation. Spine 1996; 21 (Suppl 24); 75S–78S.

Crock, HV. Internal Disco Disruption: A Challenge to Disc Prolapse 50 Yers On. Spine 1986; 11:650–653.

Dunlop RB, Adams MA, Hutton WC. Disc Space Narrowing and the Lumbar Facet Joints. J Bone Joint Surg 1984; 66B: 706–710.

Enker, P. Steffee A., McMillin C., Keppler L., Biscup R., Miller S. Artificial Disc Replacement. Preliminary Report with a 3–Yr. Minimum Follow–Up. Spine 1993; 18:1061–1070.

Finneson BE. Low Back Pain. Philadelphia: Lippincott, 1973: 144–145.

Frymoyer, JW., Kats–Baril W., Overview of Incidences and Costs of Low Back Pain. Ortho Clin. of North Am. 1911; 22:263–271.

Frymoyer, JW, Hanley, EN Jr., Howe J., Kuhlmann D., Matteri, RE. A Comparison of Radiographic Finding in Fusion and Nonfusion Patients 10 or More Years Following Lumbar Disc.

Garfin SR, Ozanne S. Spinal Pedicle Fixation. In Weinstein JN, ed. Clin Efficacy & Outcome in the Diagnosis & Treatment of Low Back Pain. NY: Raven, 1992: 137–174.

Glazer PA. New Developments in Spinal Surgery: Intervertebral Disc Replacement. Harvard Orthopaedic Journal 2000.

Goel VK et al. Kinematics of the Whole Lumbar Spine: Effect of Discectomy. Spine 1985, 10: 543–554.

Goel VK et al. Mechanical Properties of Lumbar Spinal Motion Segments as Affected by Partial Disc Removal. Spine 1986; 11: 1008–1012.

Gotfried Y et al. Facet Joint Changes After Chemonucleolysis–Induced Disc Space Narrowing. Spine 1986; 111: 944–950.

(List continued on next page.)

Primary Examiner—Eduardo C. Robert
Assistant Examiner—David Comstock
(74) Attorney, Agent, or Firm—Jonathan D. Feuchtwang; Zimmer Technology, Inc.

(57) ABSTRACT

A spinal disc prosthesis used to replace a natural human spinal disc that has been damaged by trauma or disease and a method of using the same. The spinal disc of the present invention includes, in one form thereof a flexible fluid filled nucleus, a flexible braided fiber annulus, and a pair of woven metallic end-plates comprising micro-fixation means for initial fixation to adjacent bone and a bone in-growth surface, wherein the spinal disc comprises a generally anatomic structure and shape.

24 Claims, 11 Drawing Sheets

OTHER PUBLICATIONS

Hanley EN JR. The Cost of Surg. Intervention for Lumbar Disc Herniation. In Weinstein JN ed. Clin. Efficacy & Outcome in the Diag. & Treat. of Low Back Pain NY: Raven 1992: 125.

Harris RI et al. Acquired Spondyloysis as a Sequel to Spine Fusion. J Bone Joint Surg. 1963: 45A: 1159–1170.

Hedman TP et al. Design of an Intervertebral Disc Prosthesis. Spine 1991; 16(Suppl 6):S256–260.

Hutter, CG. Spinal Stenosis and Posterior Lumbar Interbody Fusion: Clin Orthop 1985; 193: 103–144.

Keller RB. Tracing Phys. Practice: Small Area Analy. Techn. In Weinstein JN, ed. Clin. Efficacy to Outcome in the Diag. & Treat. of Low Back Pain. NY: Raven 1992: 1–7.

Kelsey JL et al. Epidemiology of Low Back Pain. Spine 1980; 5: 133–142.

Kirkaldy–Willis WH, et al. Pathology and Pathogenesis of Spondylosis and Stenosis. Spine 1978; 3: 319–328.

Kostuik JP, Intervertebral Disc Replacement In: Bridell KH et al. eds. The Textbook of Spinal Surgery, 2nd ed. Philadelphia: Lippincott–Raven, 1997: 2257–2266.

Kuslick SD, et al. The Bagby & Kuslich Method of Lumbar Interbody Fusion. Hist., Tech. & 2yr FollowUp Results of a U.S. Prospective, Multicenter Trial. Spine 1998; 23: 1267.

Lee CK, Accelerated Degeneration of the Segment Adjacent to a Lumbar Fusion. Spine 1099; 13: 375–377.

Lehmann TR et al. Long–Term Follow–Up of Lower Lumbar Fusion Patients. Spine 1987; 12:97–104.

Leong JCY et al. Long–Term Results of Lumbar Invertebral Disc Prolapse. Spine 1983; 8: 793–799.

Zucherman, JF et al. Failed Posterior Lumbar Interbody Fusion. In: White AH et al. Lumbar Spine Surgery: Techniques & Complications. St. Louis: CV Mosby. 1987: 296–305.

McConnaughey J. Artificial Discs Aid Bad–Back Sufferers. Amarillo Globe–News. http://amarilonet.com/stories/111700/us_discsaid.shtml Jul. 12, 2001.

McCulloch JA. Focus Issue on Lumbar Disc Herniation: Macro–and Microdisectomy. Spine 1996; 21 (Suppl 24) 45S–56S.

Nordby EJ. A comparison of Discectomy and Chemonucleolysis. Clin Orhop 1985; 200: 279–283.

Ray CD. Threaded Titanium Cages for Lumbar Interbody Fusions. Spine 1997; 22: 667–680.

Rutkow IM. Orthopaedic Operations in the Untied States, 1979 through 1983. J Bone Joint Surg 1986; 68A: 716–719.

Schneck CD. The Anatomy of Lumbar Spondylosis. Clin Orthop 1985; 193: 20–37.

Smith GW, et al. The Treatment of Certain Cervical–Spine Disorders by Anterior Removal of the Intervertebral Disc and Interbody Fusion. J Bone Joint Surg 1958; 40A: 607–624.

Spine Dr. Spine Surgery for the Next Millennium. http://www.spine–dr.com/surgery/edge.article2.html. Jul. 10, 2001.

Tibrewal SB et al. A Persp. Study of Lumbar Spinal Movements Before & After Discectomy Using Biplaner Radiography:Correl. of Clin. & Radiographic Findings. Spine 1985; 10:4554.

Traynelis VC et al. Spinal Disc Replace: the Dev. of Artificial Discs. Spine Universe http://www.spineuniverse.com/lp/ejournald/dp_04001traynelis_dic_replace.html. Jul. 0,2001.

Vaughan PA, et al. Results of L4–L5 Disc Excision Alone Versus Disc Excision and Fusion. Spine 1988; 13:690–695.

Vernon–Roberts B. et al. Degenerative Changes in the Intervertebral Discs of the Lumbar Spine & Their Sequelae. Rheumatol. Rehab 1977; 16:13–21.

Waddell G. Low Back Pain: a Twentieth Century Health Care Enigma. Spine 1996; 21(24): 2820–2825.

Watkins RG. Res. of Anterior Interbody Fusion In: White Ah et al. eds. Lumbar Spine Surg Tech. & Complications. St. Louis: CV Mosby 1987: 408–432.

White AA et al. Clinical Biomechanics of the Spine. 2nd ed. Philadelphia: JB Lippincott, 1990.

Yuan Ha, et al. A Historical Cohort Study of Pedical Screw Fixation in Thoracic, Lumbar & Sacral Spine Fusions. Spine 1994; 19 (Suppl 20): 2279S–2296S.

Cyrolife, Inc. Advances Development of an Injectable Spinal Disc Replacement Device. Business Week Online 2001.

* cited by examiner

ARTIFICIAL SPINAL DISC

BACKGROUND

1. Field of the Invention

The present invention relates to spinal disc prostheses used to replace human spinal discs damaged by trauma or disease.

2. Description of the Related Art

As humans age, the water content of the nuclei in their spinal discs decreases. At the same time, the collagen content of the nuclei increases; such disc degradation results in a more rigid nucleus that is more like the surrounding annulus. These changes in the disc can make the annulus more prone to traumatic injuries, such as circumferential tears. Multiple tears in an annulus can create a "gap" through which the nucleus can escape. This is event is commonly referred to as a herniated disc, which causes pain as the displaced nucleus presses against adjacent nerves.

Disc degradation also disrupts the loading patterns within the spine. Moreover, experts have observed a direct correlation between disc degradation and the formation of laterally growing osteophytes which can result in pressure being applied to adjacent neural tissue. Generally, disc degradation ultimately results in pain. Most frequently, the degradation occurs in the lumbar region (lower back) of patients and results in sciatica, a pain that begins in the lower back an travels down the sciatic nerve in the leg.

There are two standard surgical procedures used to treat problems associated with intervertebral (or spinal) disc degradation; these are discectomy and arthrodesis. Discectomy is the removal of part or all of a spinal disc. The procedure involves the removal of disc material that may be impinging on surrounding nerves, thereby relieving any associated lower back or leg pain. However, discectomies can sometimes result in redistributed spinal loading stresses, post operative spinal instability, or other problems. Some statistics report that although 48% to 86% of discectomies are initially successful, i.e. the patient experiences no more pain after surgery, the pain often returns over time. Ten years after surgery 60% to 70% of patients experience back pain again, and 25% to 30% have recurrent sciatica.

Arthrodesis (or spinal fusion) is another common surgical treatment for spinal disc degradation problems. Spinal fusion is used to prevent the spine from moving in a specific area of the spine and is often performed in conjunction with a discectomy. The procedure increases the stability of a patient's spine around affected vertebrae of a damaged or removed disc, and prevents further degradation of the treated area.

Between 50% and 94% of patients have good to excellent results immediately after arthrodesis[1]. However, years after surgery problems can arise including spinal stenosis, vertebral osteophyte formation, and disc degeneration adjacent to the treated location. These problems generally result in a return of pain.

A need exists, therefore, for a method for and means of treating spinal disc degradation and related problems that reduces or eliminates the long term problems associated with presently employed treatments, such as discectomy or arthrodesis. Those of skill in the art have realized that a solution to the problems described above requires a prosthetic spinal disc. A viable prosthetic disc may result in a variety of additional benefits including shorter patient recovery time, a decrease in number of people who experience chronic back pain, and a decrease in revision spinal fusions. Generally, those of skill in the art employ one of three prosthetic disc design concepts, all of which have disadvantages that ultimately limit there success. These concepts include nucleus replacement, mechanical discs, and composite discs.

Nucleus replacement involves removal and replacement of a damages nucleus. This approach assumes that the annulus and end-plates are uncompromised. Consequently, nucleus replacement is useful only during the early stages of disc degeneration where minimal segment collapse has occurred. Also, nucleus replacement requires placing a hole in the annulus to insert the prosthetic nucleus. Because the prosthetic nucleus is thereafter unsecured, it is sometimes ejected from the disc through the hole.

Mechanical discs and composite discs, the second and third disc replacement concepts, generally comprise a polymer center bounded by metallic end-plates having growth promoting surfaces for long term fixation to surrounding bone and prongs or spikes to accommodate short term fixation to the same. These discs require a relatively invasive surgical procedure in which a large incision is made directly anterior to the affected area, and a path is generated between the anterior incision and desired surgical location. Furthermore, mechanical and composite discs generally comprise parallel end-plates, which do not correspond to natural end-plates which normally have non-parallel adjacent vertebrae. This inconsistency between prosthetic discs known to those of skill in the art and natural discs may result in loading and deformation problems for a patient's spine.

Thus, a need exists for an artificial spinal disc and method of using the same for treating disc degradation and related problems that restores or maintains the spinal function at all stages of disc degeneration.

A further need exists for an artificial spinal disc and method of using the same for treating disc degradation and related problems, wherein the disc includes a prosthetic analog for each component of a natural disc.

A further need exists for an artificial spinal disc and method of using the same for treating disc degradation and related problems that can be employed in a manner that is minimally invasive to the patient.

A still further need exists for an artificial spinal disc and method of using the same for treating disc degradation and related problems that employs a more anatomically correct prosthetic disc.

SUMMARY

The present invention, in one form thereof, is a prosthetic artificial disc comprising an annulus, a nucleus, and a pair of endplates. The prosthetic disc of the present invention is expandable such that it may be inserted into a patient's body in a minimally invasive manner.

The present invention, in broad terms, comprises an expandable, generally ring shaped annulus having, when expanded, the shape, functional properties and mechanical properties of a natural spinal disc annulus. The annulus surrounds a prosthetic spinal disc nucleus. The nucleus of the present invention comprises an expandable shell, having, when expanded, the shape, functional properties and mechanical properties of a natural spinal disc nucleus. Finally, the invention comprises a pair of flexible spinal disc endplates that are attached superiorly and inferiorly to the prosthetic annulus, thereby containing the prosthetic nucleus within the annulus. The endplates provide stability to the prosthetic disc and a means of fixation to vertebra that are adjacent to the treated area.

The present invention further comprises a method of inserting a prosthetic spinal disc in a human body using relatively less invasive techniques than prior art surgical methods.

An advantage of the present invention is that the disc of the present invention is useful in treating disc degradation and related problems, and it restores or maintains spinal function at all stages of disc degeneration.

Another advantage of the present invention is that the disc of the present invention includes a prosthetic analog for each component of a natural disc.

Yet another advantage of the present invention is that it can be used in treating disc degradation and related problems in a manner that is minimally invasive to the patient.

A still further advantage of the present invention is that it employs a more anatomically correct prosthetic disc.

These and other advantages and features of the present invention will be apparent to those skilled in the art upon a review of the appended claims and drawings.

BRIEF DESCRIPTION

The above-mentioned and other features and objects of this invention, and the manner of obtaining them, will become more apparent and the invention itself will be better understood by reference to the following description of an embodiment of the invention taken in conjunction with the accompanying drawings, wherein.

Corresponding reference characters indicate corresponding parts throughout the several views. Although the drawings represent an exemplary embodiment of the present invention, the drawings are not necessarily to scale and certain features may be exaggerated to better illustrate and explain the invention. The exemplification set out herein illustrates an exemplary embodiment of the invention only.

DETAILED DESCRIPTION

As used herein, the following definitions of direction apply. Anterior and posterior mean nearer the front or nearer the back of the body respectively. Thus, for the spinal disc described herein, anterior refers to that portion of the disc that is nearer the front of the body. Proximal and distal mean nearer to or further from the root of the structure, respectively. For example, the distal spine is closer to the feet, and the proximal spine is closer to the head. The adjectives medial and lateral mean nearer the median plain or further from the median plain respectfully. The median plain is an imaginary vertical plane through the middle of the body that divides the body into right and left halves.

The present invention relates to prosthetic or artificial disc implants. The invention described herein can be used to replace spinal discs damaged by injury or disease. Although the invention is described herein with reference to a human spinal disc, those skilled in the art will appreciate that the disclosure and appended claims of the present invention are also applicable to any vertebral animal.

Figures 1, 2:
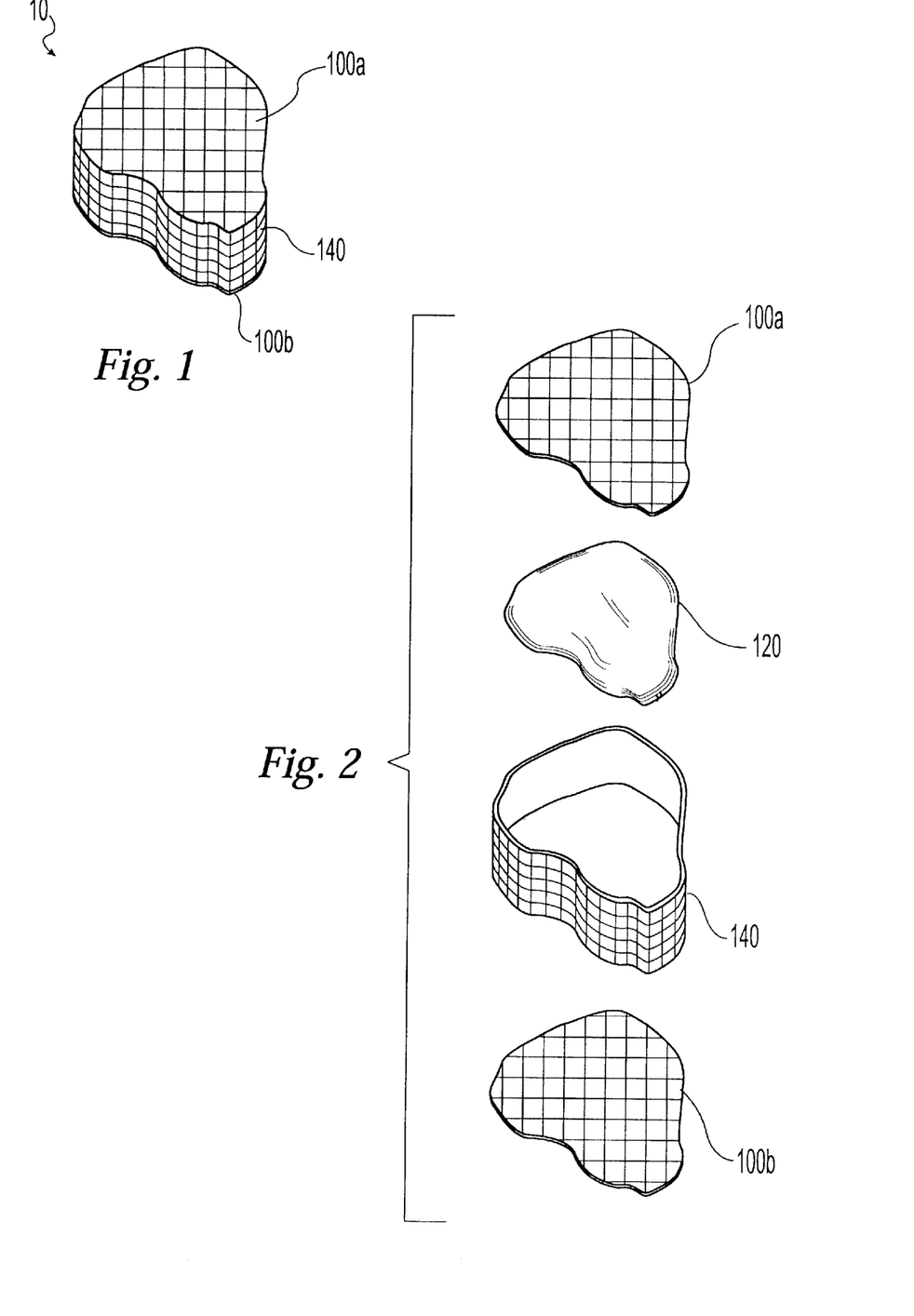
FIG. 1 is a perspective view of a prosthetic spinal disc in accordance with the present invention.
FIG. 2 is an exploded perspective view of the disc in FIG. 1.

Referring initially FIGS. 1 and 2, there is shown a perspective view and an exploded perspective view, respectively, of a prosthetic spinal disc according to the present invention. The disc comprises an anatomically shaped superior endplate 100a, an expandable nucleus 120, a compressible annulus 140, and an inferior anatomically shaped endplate 100b.

Figure 3:
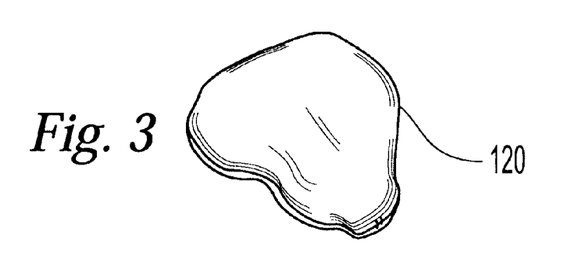
FIG. 3 is a perspective view of a spinal disc nucleus according to the present invention in a deflated state.

Referring now to FIG. 3, there is shown a perspective view of prosthetic nucleus 120. Nucleus 120 comprises a flexible or an expandable bag having an exterior surface and a hollow interior. As used herein, the word "flexible" shall mean a deformable construct capable of being compressed such that the construct occupies less than the maximum amount of volume theoretically possible for the construct. The word "expandable" shall be inclusive of the word flexible, but shall also refer to constructs whose external surface area can be increased significantly by increasing the internal pressure of the construct, for example by filling such internal area with a desired fluid. The word "inflatable" shall refer to constructs that can be filled with a fluid until the flexible or expandable construct assumes a final volume or shape. Nucleus 120 is constructed of a biocompatible fabric material having suitable strength and resistance to tearing to accept the dynamic loading required of a spinal disc. Nucleus 120 preferably comprises a woven polymer material such as polyethylene, polyamide, polypropylene, polyester, polycarbonate, polysulfone, polymethylmethacrylate, or alternatively fibrous hydrogel or glass. Nucleus 120 may further comprise ceramic fibers for reinforcement.

Figure 4:
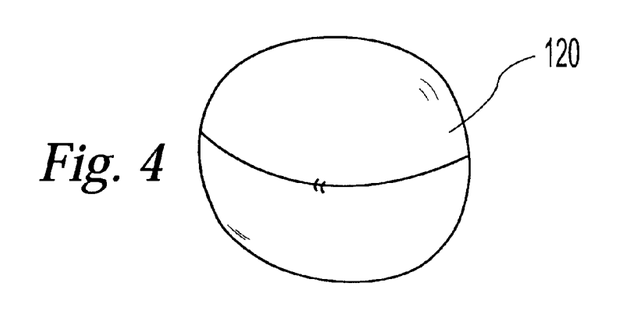
FIG. 4 is a perspective view of a spinal disc nucleus according to the present invention in an inflated state.

As shown in FIG. 4, nucleus 120 is inflated, as such term is used herein, to a final desired size. Nucleus 120 is constructed such that when inflated it is capable of being contained within the center of annulus 140 (described herein below) and between endplates 100*a* and 100*b* (also described herein below). In its inflated state, nucleus 120 preferably occupies substantially all of the space within the center of annulus 140 and bounded by endplates 100*a* and 100*b*.

Figure 5:
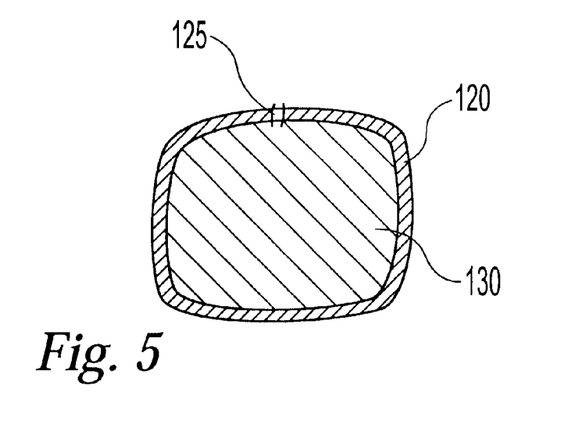
FIG. 5 is a side elevational cross-sectional view of a spinal disc nucleus according to the present invention in an inflated state.
Figure 6:
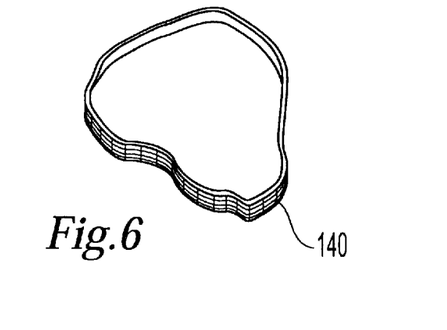
FIG. 6 is a perspective view of a deflated spinal disc annulus according to the present invention.

Referring now to FIG. 5, there is shown a side cross-sectional view of an inflated nucleus 120. In its inflated state, nucleus 120 is filled with a fluid 130 having the mechanical properties of a natural spinal disc nucleus. Suitable fluids for filling or inflating nucleus 120 include polyethylene, polyamide, polypropylene, polyester, polycarbonate, polysulfone, polymethylmethacrylate, hydrogel, and silicone rubber. Preferably, the fluid will comprise a "hydrogel" having the mechanical properties listed above for natural disc nuclei.

In order to inflate nucleus 120, access portal 125 is disposed through the wall of nucleus 120, as shown in FIG. 5. Portal 125 comprises a bore, of any desired shape, wherein said bore is in communication between the exterior surface of nucleus 120 and the interior of nucleus 120. Fluid 130, as shown in FIG. 5 is placed through portal 125 by any desired means, such as by injecting or pumping, until fluid 130 has substantially filled the entire interior of nucleus 120 and inflated the same to a final desired shape or volume suitable such that nucleus 120 will be usable in a prosthetic disc. Portal 125 preferably comprises a unidirectional valve such that fluid 130 will not pour out. Alternatively annulus 140 (described below) will prevent any back flow of fluid 130 from nucleus 120.

Figure 7:
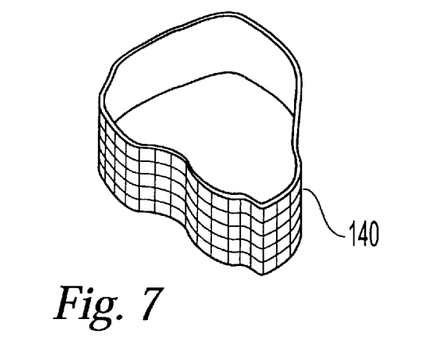
FIG. 7 is a perspective view of an inflated spinal disc annulus according to the present invention.
Figure 8:
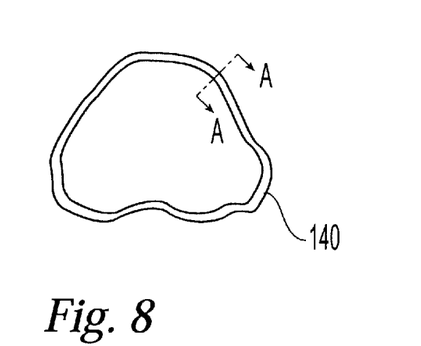
FIG. 8 is a top view of a spinal disc annulus according to the present invention.
Figure 9:
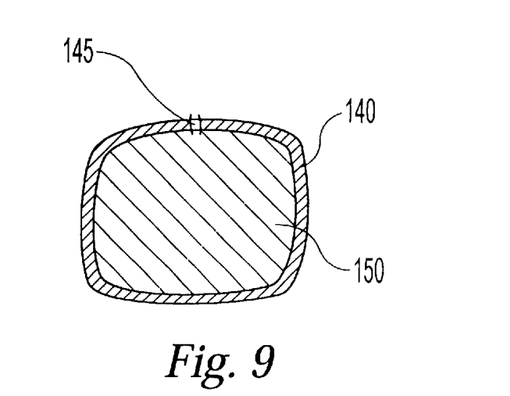
FIG. 9 is a side cross-sectional view of a spinal-disc annulus according to the present invention.

Turning now to FIGS. 6 through 9, there is shown a flexible, prosthetic, spinal disc annulus 140 according to an exemplary embodiment of the present invention. As shown in FIGS. 7–9, when expanded, annulus 140 comprises a ring like shape having an inner area suitable to enclose nucleus 120. Annulus 140 further comprises an exterior surface and an interior, as shown in FIG. 9, thereby forming a hollow portion within annulus 140.

The ring shape of annulus 140 preferably approximates the anatomical shape of a natural spinal disc annulus, as shown in FIG. 8. When deflated, FIG. 6, annulus 140 is more flexible such that it may be compressed and inserted through a relatively small incision or path.

Annulus 140 is constructed of a biocompatible material having suitable strength and other mechanical properties in its inflated state to resist detrimental spinal movement in the same manner as a natural spinal disc annulus. Annulus 140 preferably comprises a polymer material such as polyethylene, polyamide, polypropylene, polyester, polycarbonate, polysulfone, polymethylmethacrylate, or alternatively fibrous hydrogel or glass. Annulus 140 may further comprise ceramic fibers for reinforcement.

In addition, as shown in FIG. 1 and FIG. 2, annulus 140 is preferably constructed by weaving or braiding a fibrous form of the polymer material in a manner known to those of skill in the art of making flexible or expandable polymer containers.

Figure 10:
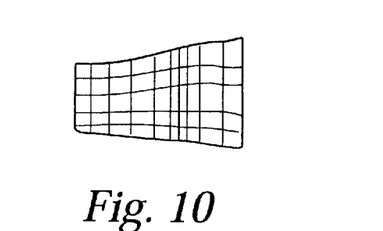
FIG. 10 is a side elevational view of a spinal disc annulus according to the present invention.

Referring to FIGS. 7 and 8, annulus 140 is flexible and inflatable, as such terms are used herein, to a final desired size and shape. Annulus 140 is constructed such that when inflated it assumes a slanted shape, when viewed medially or laterally, from the side as shown in FIG. 10.

Referring again to FIGS. 1 and 2, there is shown annulus 140 fixedly attached to flexible endplates 100*a* and 100*b* (described below in greater detail) such that annulus 140 remains attached to endplates 100*a* and 100*b* as it is inflated. Ultimately, endplates 100*a* and 100*b* and annulus 140 form the semi-rigid external portion of a prosthetic disc having nucleus 120 disposed within the center of annulus 140 and between endplates 100*a* and 100*b*.

Referring now to FIG. 9, there is shown a side cross-sectional view of inflated annulus 140. In its inflated state, annulus 140 is filled with an initially fluid material 150 that becomes semi-rigid as it cures. Depending on the material, curing may be accomplished by any means known in the art, such as inserting another material, applying heat, exposing to air, or merely allowing enough time to pass. Upon curing, the material should have the mechanical properties of a natural spinal disc annulus. In an alternative embodiment fluid 150 does not cure. In this embodiment, annulus 140 is sufficiently interwoven, that upon inflation with fluid 150, annulus 140 is sufficiently internally pressurized to assume the material properties of a natural spinal disc annulus. Suitable fluids for filling or inflating annulus 140 include polyethylene, polyamide, polypropylene, polyester, polycarbonate, polysulfone, polymethylmethacrylate, hydrogel, and silicone rubber. Preferably, the fluid will comprise a "hydrogel" having the mechanical properties listed above for natural disc annulus.

Referring now to FIG. 9, there is shown a side cross sectional view of annulus 140, taken along line A—A in FIG. 8. Annulus 140 further comprises access portal 145 and aperture 146. In order to inflate annulus 140, access portal 145 is disposed through the wall of annulus 140, as shown in FIG. 9. Portal 145 comprises a bore, of any desired shape, wherein said bore is in communication between the exterior surface of annulus 140 and the interior of annulus 140. Fluid 150, as shown in FIG. 9 is placed through portal 125 by any desired means, such as by injecting or pumping, until fluid 150 has substantially filled the entire interior of annulus 140 and inflated the same to its final desired shape, i.e. a prosthetic annulus having an anatomical shape.

Figure 24:
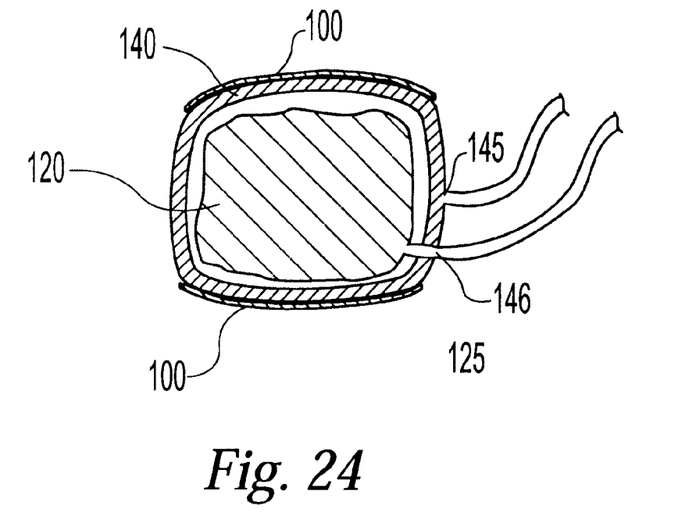
FIG. 24 is a perspective view of a spinal disc according to the present invention with a pair of adjacent filling tubes attached thereto.
Figure 25:
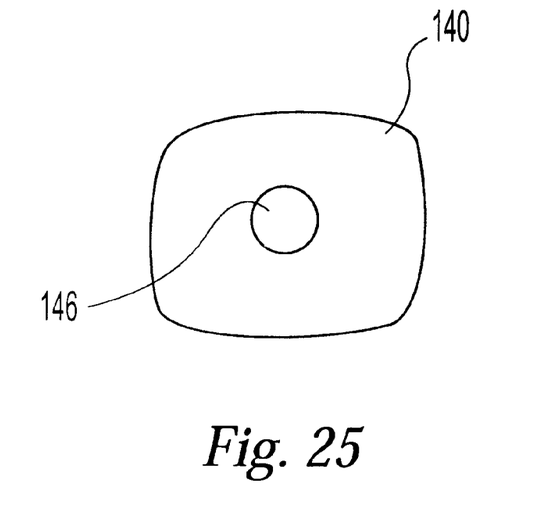
FIG. 25 is another view of spinal disc annulus according to the present invention.

As stated supra, annulus 140 further comprises aperture 146. Aperture 146 is disposed through the wall of annulus 140 such that access portal 125 of nucleus 120 can extend there through, as shown in FIG. 24. Thus, nucleus 120 and annulus 140 may both be inflated as desired. This process is described more fully later in this section of the application.

Figure 11:
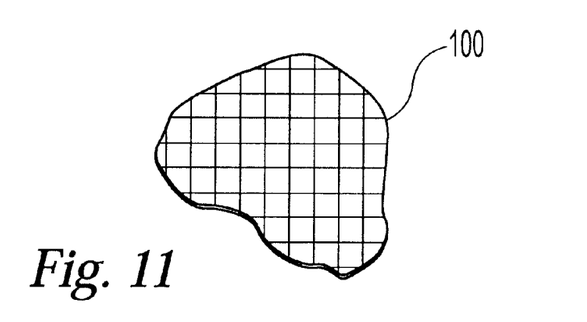
FIG. 11 is a perspective view of a spinal disc end-plate according to the present invention.

Turning now to FIG. 2, there is shown a pair of prosthetic endplates 100*a*, 100*b* (collectively endplate 100) for use with prosthetic spinal disc 10. FIG. 11 shows a perspective view of endplate 100. Endplate 100 is flexible and preferably comprises woven or braided metal fibers, wherein the fibers are selected from the group consisting of titanium, tantalum, cobalt chrome alloy, stainless steel and nitinol. Alternatively, endplate 100 could comprise a polymer or ceramic material in a form that provides a flexible pad having mechanical properties similar to those of a natural spinal disc endplate.

Figure 12:
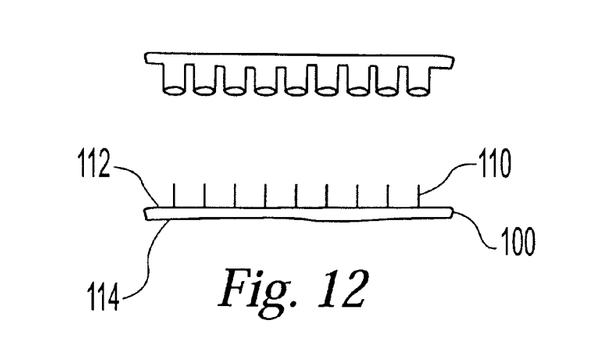
FIG. 12 is a side elevational view of a spinal disc end-plate according to the present invention.
Figure 13:
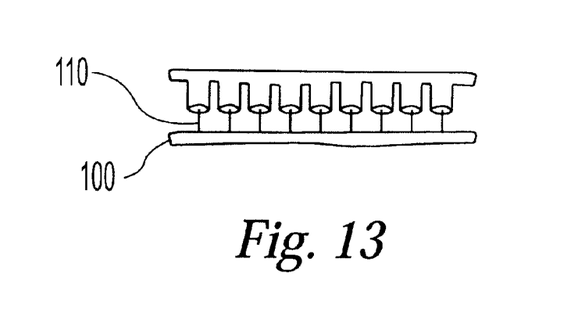
FIG. 13 is a side elevational view of the initial fixation means between an end-plate and cancellous bone.

Referring now to FIG. 12, there is shown an exaggerated side elevational view of endplate 100 and adjacent cancellous bone. During a disc replacement surgery, the physician will remove the patient's natural disc then surgically remove some of the cortical bone from the surrounding vertebra, thereby exposing the underlying cancellous bone. Endplate 100 comprises bone contacting surface 112 and annulus contacting surface 114. When prosthetic disc 10 is inserted into a vertebral space during a spinal disc replacement surgery, bone contacting surface 112 is disposed against the exposed cancellous bone of adjacent resected superior and inferior vertebrae.

It is necessary for a prosthetic spinal disc to achieve good initial fixation of the implant immediately upon implantation. Compressive forces in the spine assist with fixation, but there is still a risk of lateral, medial, posterior or anterior displacement of disc 10 upon its implantation. Consequently, a need exists for a means of short term spinal disk fixation.

In most joint arthroplasties, initial fixation is accomplished by the appropriate placement of surgical screws until long term fixation, often through bone growth into the implant, can be established. However, because of nerves and other anatomical obstructions, it is difficult to surgically access an intervertebral space, and screws may damage surrounding nerves or other soft tissues. Consequently, most prosthetic discs comprise a group of prongs that protrude from the bone contacting surface of the endplate and insert into adjacent cancellous bone to establish initial fixation, a system referred to herein as "macrofixation." Macrofixation, however, requires the vertebral space to be spread far enough during insertion of the prosthesis to accommodate the prongs. This action can result in a more traumatic surgery for the patient.

In the present invention, bone contacting surface 112 of prosthetic disc 10 comprises a plurality of miniature protrusions 110, wherein each protrusion 110 comprises one or more fibers that extend vertically from bone contacting surface 112 of endplate 100. Preferably, protrusions 110 are formed during the process in which endplate 100 is fabricated. Upon placement of prosthetic disc 10, protrusions 110 extend into the tube like pores of the adjacent cancellous bone, thereby preventing the disc from moving laterally, medially, anteriorly, or posteriorly. This type of initial fixation is referred to herein as "microfixation."

Endplate 100 further comprises a porous structure such that bone can grow into endplate 100 to provide long term fixation of the disc. Endplate 100 can comprise any biocompatible metal. However, titanium, which works well as a bone contacting surface, is preferred. It is further preferred for endplate 100 to have a superior to inferior thickness of at least 1 millimeter to allow for maximum bone growth into the endplate and, therefore, maximum fixation of disc 10.

Figure 14:
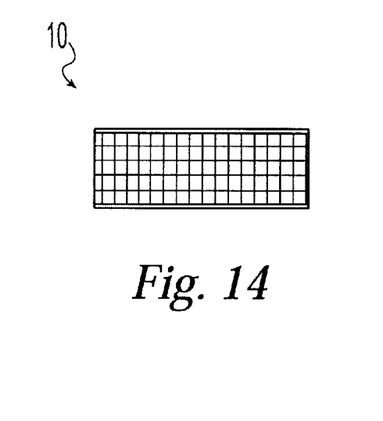
FIG. 14 is a side elevational view of the disc of FIG. 1.

Referring still to FIG. 12, endplate 100 further comprises annulus contacting surface 114. As shown in FIG. 14, annulus 140 is fixedly attached to endplates 100*a* and 100*b* such that the combination of components is mutually flexible and such that annulus 140 remains inflatable. Upon inflation of annulus 140, as shown in FIG. 14, endplates 100*a* and 100*b* are not parallel. Instead, they are in a more anatomically correct orientation.

Figure 15:
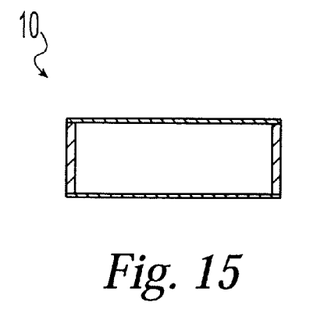
FIG. 15 is a side cross-sectional view of a prosthetic spinal disc according to the present invention.
Figure 16:
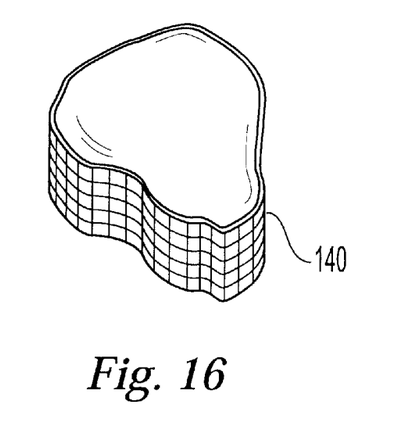
FIG. 16 is a side cross-sectional view of an alternative embodiment of a prosthetic spinal disc according to the present invention.
Figure 17:
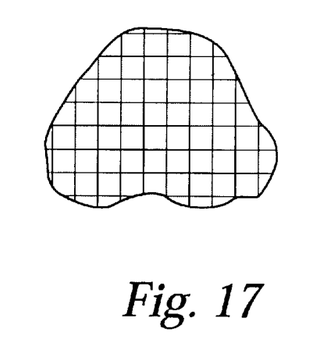
FIG. 17 is a top view of the disc of FIG. 1.

Nucleus 120 is disposed within the center of annulus 140 and between endplates 100*a* and 100*b*. Nucleus 120 is preferably expandable and free floating within this space, as shown in FIG. 15. Alternatively, a flexible nucleus may be employed, wherein said nucleus is attached to annulus contacting surface 112 of endplates 100*a* and 100*b* and to the inner diameter of annulus 140, as shown in FIG. 16.

Figure 18:
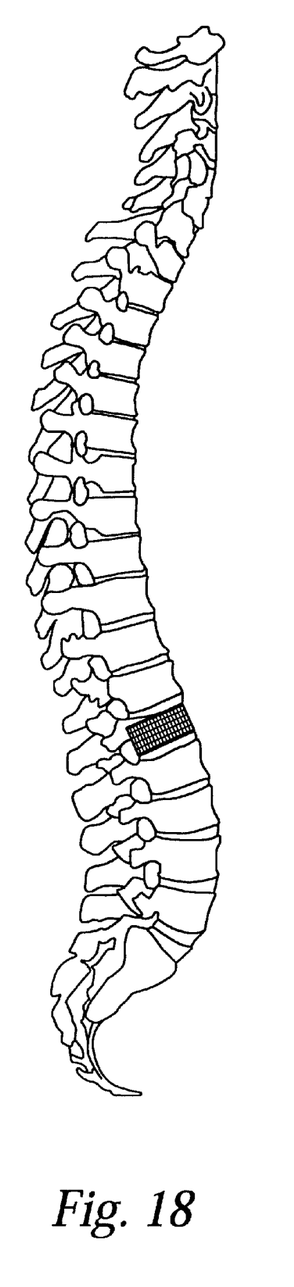
FIG. 18 is a side elevational view of the disc of FIG. 1 inserted into a human vertebral space.
Figure 19:
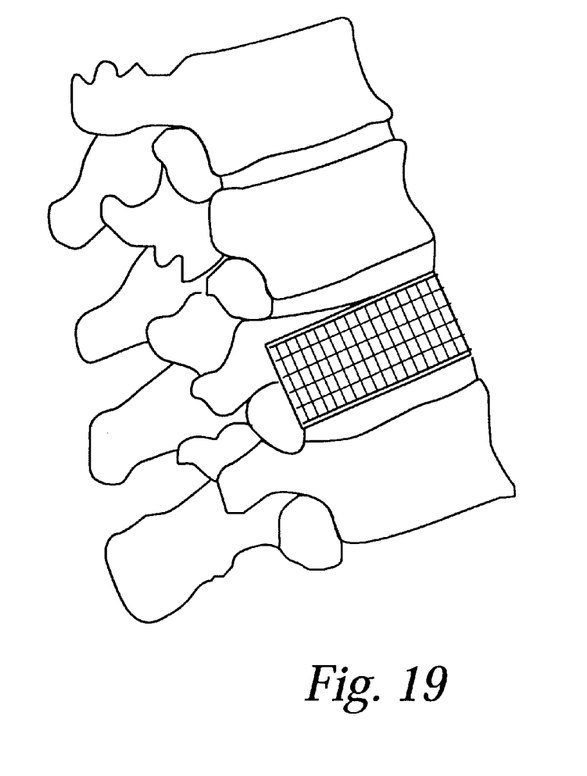
FIG. 19 is an enlarged view of FIG. 18.

The fully assembled prosthetic disc 10 of the present invention is mutually flexible such that the entire assembly can be inserted through a relatively small incision or through a relatively small surgical path. Upon being placed in the affected area, annulus 140 and nucleus 120 of disc 10 are inflated to their final respective shapes and sizes, such that disc 10 can replace the removed damaged natural disc as shown in FIGS. 18 and 19. FIGS. 18 and 19 further show a human spinal column having prosthetic disc 10, wherein disc 10 comprises endplates 100*a* and 100*b*; nucleus 120; and annulus 140.

Figure 20:
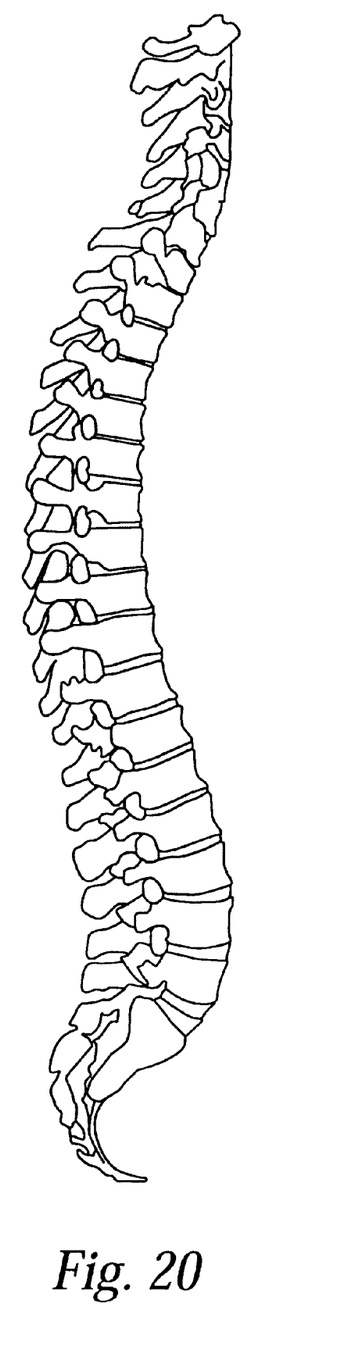
FIG. 20 is a side view of a human spine.

The present invention further comprises a method for treating problems associated with spinal disc degradation. Referring to FIG. 20, there is shown a side view of a human spine, having a damaged natural spinal disc 5. The prescribed course of treatment is a spinal disc arthroplasty according to the method of the present invention. The present method comprises, in general terms, the steps of: making an incision on the epidermis of the patient's body; creating a medically acceptable surgical path between incision 2010 and damaged disc 5; removing damaged disc 5 by surgical means known in the art, thereby creating a vertebral space; inserting an prosthetic spinal disc implant through the surgical path to the former location of damaged disc 5; and positioning and/or inflating the prosthetic spinal disc such that it is properly placed in the vertebral space.

Figure 21:
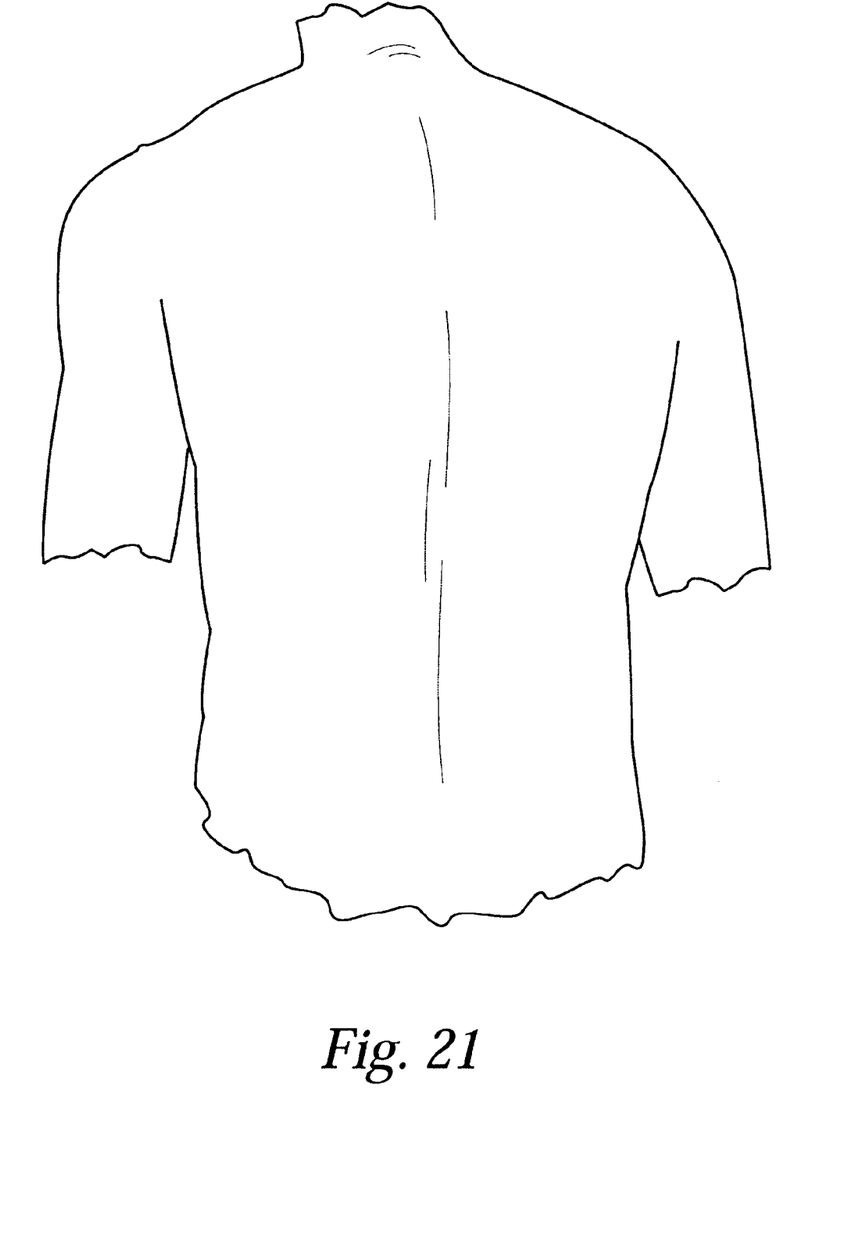
FIG. 21 is a perspective view of a human back.

Referring now to FIG. 21, there is shown a perspective view of a human back having incision 2110 made in the epidermis thereof. Incision 2110 is preferably made generally posteriorly relative to the patient. However, incision 2110 can be made in any location, from which the surgeon will be able to create a surgical path to the location of damaged disc 5, without unnecessarily damaging surrounding anatomical structures. It is desirable to make incision 2110 posteriorly because doing so allows for direct access to the damaged disc.

Figure 22:
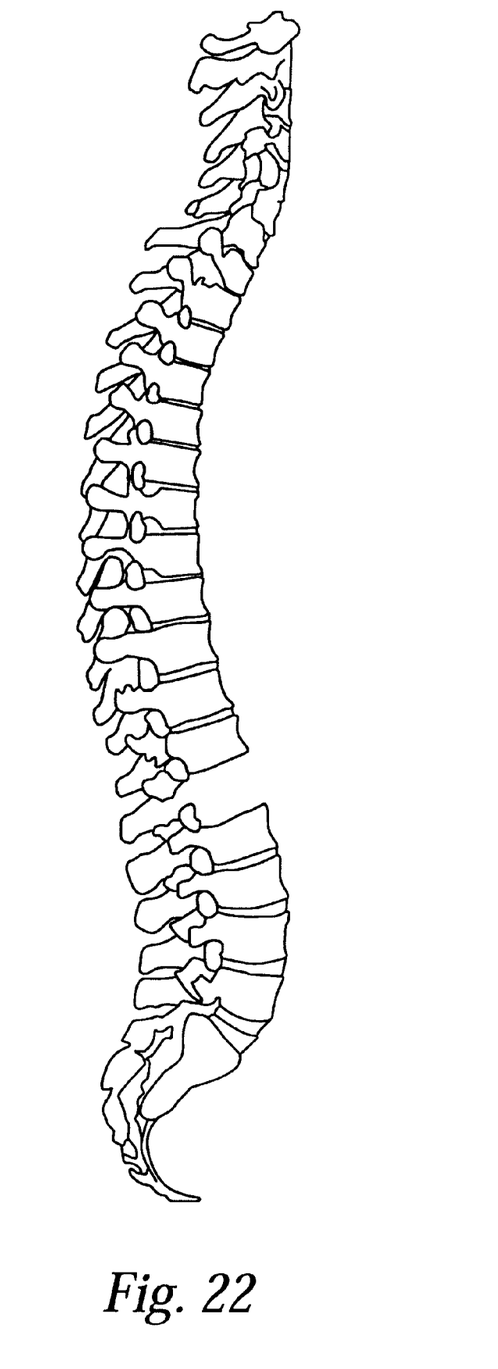
FIG. 22 is a side view of a human spine having a missing disc.

Referring now to FIG. 22, there is shown a human spine with damaged disc 5 removed therefrom. Any of a number of surgical techniques known to those of skill in the art may be used to remove damaged disc 5 from a patient's spine, including for example, a microdiscectomy.

In a microdiscectomy a small incision, 2 to 4 cm, is made in the skin over the area of the damaged disc. A path is created between the incision and the damages disc by moving muscle away from the lamina of the vertebra above and below the level of the ruptured disc. A tubular retractor is thereafter inserted through which surgical instruments and endoscopic visualization tools can be used. Using an air drill or special bone instruments enough of the lamina is removed to gain access to the disc. Using special instruments, some of the ligament under the bone is removed and the nerve root carefully moved. The damaged disc is then found and removed from in front of the nerve root. The disc space may then be entered and additional loose disk material removed.

In a disc arthroplasty, removal of damaged disc 5 is followed by the surgical implantation of a prosthetic disc. In some embodiments of the present invention, the surgeon may seek to maintain the vertebral space created by the discectomy, by employing one of various means known to those of skill in the art of spinal surgery. One exemplary means of maintaining such space is suspending the patient in a prone (face down) position such that the spine is arced, and the surgically created vertebral space is a natural occurrence of such arcing. The vertebral space may also be maintained by using any spinal retractor known to those of skill in the art. Alternatively, the surgeon may choose to forgo maintaining significant spacing, and simply insert, position, and inflate an expandable disc implant in the appropriate location.

Figure 23:
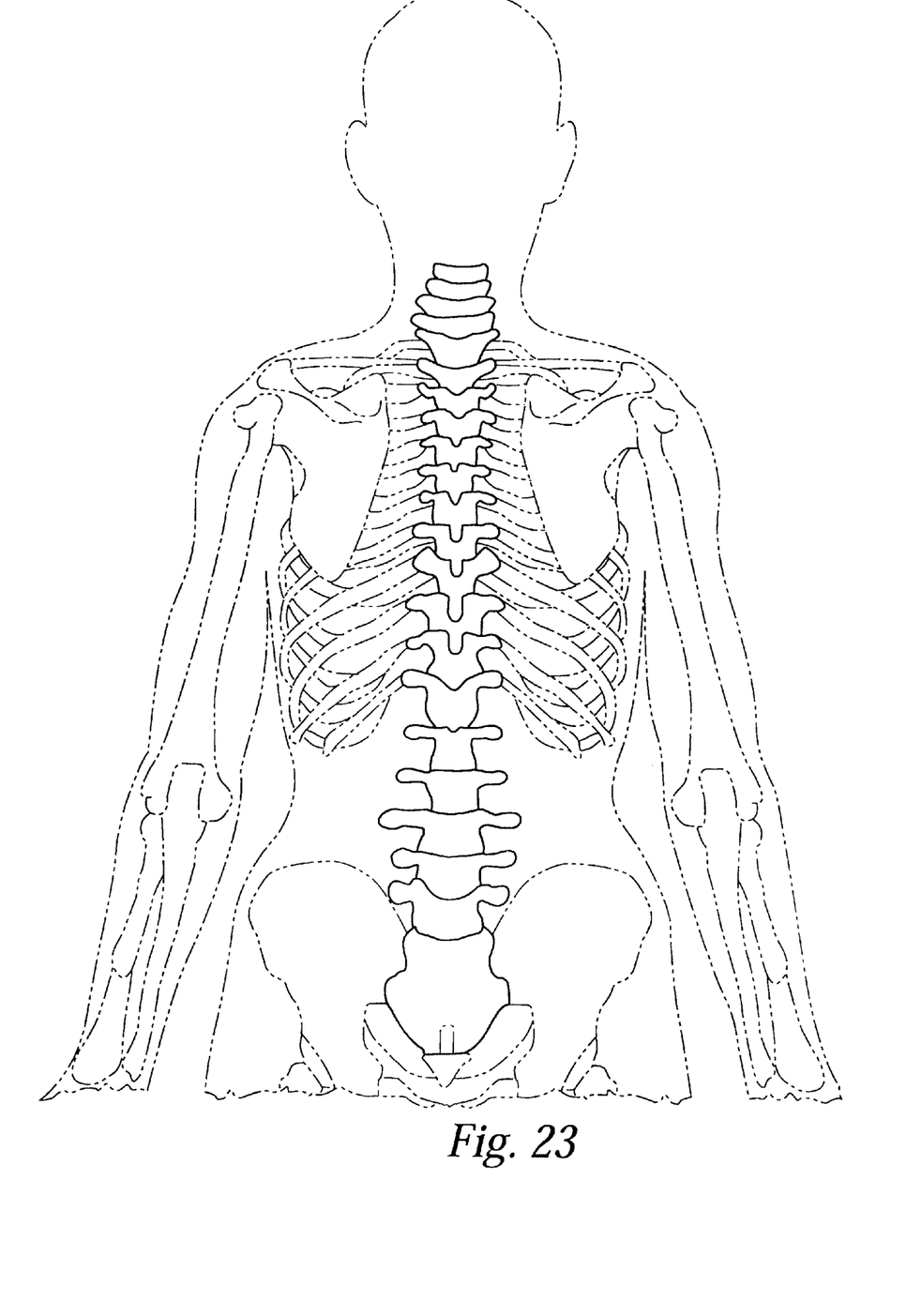
FIG. 23 is a posterior view of a human spine and the surrounding anatomy.

Insertion of a prosthetic spinal disc, further comprises using surgical instruments known to those of skill in the art are used to further resect the adjacent vertebrae, thereby exposing tubular cancellous bone to which the endplates 100 of prosthetic disc 10 may attach. Thereafter, the surgeon inserts prosthetic disc 10 into the vertebral space. It is preferred to use the same incision and path to remove the damaged natural disc and to insert the prosthetic disc to avoid additional patient trauma. In a typical disc arthroplasty, the vertebral space must be approached through an anterior incision. The reason for using an anterior approach is, as shown in FIG. 23, that the anatomy surrounding the spine prevents a safe posterior approach with a disc as large as those disclosed in the prior art. However, prosthetic disc 10 can be used in a less invasive approach, such as through a posterior incision as might be used during a microdiscectomy. Those of skill in the art will appreciate, however, that the method and apparatus of the present invention can be used through an incision located anywhere on a patient's body, as long as a path can be created between the incision and the desired surgical site.

The method of the present invention further comprises expanding a prosthetic spinal disc to its final shape. Referring now to FIG. 24, a surgeon attaches filling tubes 2320 to nucleus 120 and annulus 140, either before or after prosthetic disc 10 is inserted into a patient. Each tube 2320 comprises opposing ends 2321 and 2322. Tubes 2320 are flexible and preferably comprise a polymer that will not react with fluid 130 or fluid 150. Ends 2321 are attached to portals 125 and 145 of nucleus 120 and annulus 140, respectively. Opposing ends 2322 of tubes 2320 are attached to a means for providing fluids 130 or 150. An exemplary means comprises a pair of dedicated pumps, each pump having its own reservoir of fluid.

In the preferred embodiment, shown in FIG. 24, portal 125 and portal 145 are separate such that two distinct tubes fill nucleus 130 and annulus 140 respectively. However, those skilled in the art will appreciate that tubes 2320 might also be concentric tubes, or may be arranged in any configuration known to those of skill in the art.

After disc 10 is implanted and attached to filling tubes 2320, the surgeon, or a nurse, can inflate annulus 140 and nucleus 120 to a desired size, shape or pressure and remove retractor 2310.

Although, the method has been described herein as injecting a fluid into prosthetic disc 10 to inflate it to its final size and shape, other means might also be used to accomplish the same result. For example, the annulus and nucleus of the present invention may comprises hydrogels having various water absorption properties, such that once disc 10 is in place it may be exposed to water, thereby facilitating expansion of disc to its final shape.

In any event, after prosthetic spinal disc 10 is inserted into the affected area. The surgeon then closes the incision and the procedure is complete.

It will be appreciated by those skilled in the art that the foregoing is a description of a preferred embodiment of the present invention and that variations in design and construction may be made to the preferred embodiment without departing from the scope of the invention as defined by the appended claims.

I claim:

1. A prosthetic spinal disc, comprising:
   a prosthetic spinal disc annulus, the annulus comprising a flexible ring of desired size and shape, the ring being compressible such that it may occupy a variable volume of space, the ring comprising an exterior and a hollow interior, the ring further comprising an opening, the opening being in communication between the exterior and the interior;
   a first fluid inside the hollow interior inflating the ring to a size and shape suitable for a spinal disc annulus;
   a prosthetic spinal disc nucleus, comprising: a flexible shell having a hollow interior, the nucleus being compressible such that it may occupy a variable volume of space;
   a second fluid inside the hollow interior inflating the nucleus into a final shape, the shape being suitable for a spinal disc nucleus; and
   a pair of prosthetic spinal disc end plates, each end plate of the pair of end plates being flexible and having a relatively flat shape, each end plate having a suitable size and shape for a spinal disc, each end plate comprising a bone contacting surface and an annulus contacting surface, wherein the bone contacting surface is susceptible to bone growth therein for long term fixation to adjacent natural bone, and wherein the bone contacting surface further comprises means for initial short term fixation to adjacent bone in a desired vertebral space,
   the annulus being attached to the annulus contacting surface of each end plate of the pair of end plates, such that the nucleus is surrounded by the annulus and between the pair of end plates.

2. The spinal disc of claim 1, wherein the nucleus is attached to the annulus.

3. The spinal disc of claim 1, wherein the nucleus is attached to each end plate of the pair of endplates.

4. The spinal disc of claim 1, wherein the ring comprises a braided fibrous material.

5. The spinal disc of claim 1, wherein the ring comprises a material having the material properties of a natural annulus.

6. The spinal disc of claim 1, wherein the ring assumes an asymmetric shape.

7. The spinal disc of claim 1, wherein the ring comprises a material selected from the group consisting of polyethylene, polyamide, polypropylene, polyester, polycarbonate, polysulfone, polymethylmethylacrylate, hydrogel and glass.

8. The spinal disc of claim 1, wherein the first fluid comprises a material having the material properties of a natural annulus.

9. The spinal disc of claim 1, wherein the first fluid comprises a material selected from the group consisting of polyethylene, polyamide, polypropylene, polyester, polycarbonate, polysulfone, polymethymethylacrylate, hydrogel, and silicone rubber.

10. The spinal disc of claim 1, wherein the nucleus comprises a flexible, biocompatible material having the material properties of a natural nucleus.

11. The spinal disc of claim 1, wherein the nucleus comprises a material selected from the group consisting of polyethylene, polyamide, polypropylene, polyester, polycarbonate, polysulfone, polymethylmethylacrylate, hydrogel and glass.

12. The spinal disc of claim 1, wherein the nucleus is expandable to an asymmetric shape.

13. The spinal disc of claim 1, wherein the second fluid comprises a material having the material properties, of a natural nucleus.

14. The spinal disc of claim 1, wherein the metal is selected from the group consisting of titanium, tantalum, stainless steel, nitinol, and cobalt chrome alloy.

15. The spinal disc of claim 1, wherein end plates comprise woven biocompatible metal fibers.

16. The spinal disc of claim 1, wherein the means for initial short term fixation to adjacent bone comprises a plurality of projections extending from the bone contacting surface of the end plate, the projections being small enough to fit within the pores of adjacent cancellous bone, thereby providing intial interior to posterior and lateral to medial fixation of the disc.

17. The spinal disc of claim 1, wherein the second fluid comprises a material selected from the group consisting of polyethylene, polyamide, polypropylene, polyester, polycarbonate, polysufone, polmethylmethylacrylate, hydrogel, and silicone rubber.

18. A method of implanting a prosthetic spinal disc comprising the steps of:

making an incision through the epidermis of a person;

creating a surgical path from the incision to the natural disc;

removing the natural disc, thereby creating a vertebral space having adjacent vertebra;

resecting the vertebra such that cancellous bone is exposed thereon;

inserting a prosthetic spinal disc comprising an expandable nucleus, an expandable annulus and a pair of flexible end plates;

inflating the prosthetic disc to a final desired shape;

wherein the step of inflating the prosthetic disc comprises filling the nucleus with a first fluid and filling the annulus with second fluid.

19. The method of claim 18, wherein the incision measures about 2 to 4 cm.

20. The method of claim 18, wherein the first fluid and the second fluid are the same.

21. The method of claim 18, wherein the first fluid and the second fluid are selected from a group consisting of polyurethane, hydrogel, polysulfone, polyaryletherketone, polycarbonate, clastomer, and silicone rubber.

22. The method of claim 21, wherein the first and second fluids further comprise ceramic fibers.

23. The method of claim 18, wherein the step of making an incision comprises making a posterior incision relative to the patient.

24. The method of claim 18, wherein the step of inflating the prosthetic disc comprises exposing the disc to water.

* * * * *